United States Patent [19]

Fischer et al.

[11] 3,954,804

[45] May 4, 1976

[54] PRODUCTION OF HIGH MOLECULAR WEIGHT UNSATURATED KETONES

[75] Inventors: Roman Fischer, Ludwigshafen; Norbert Goetz, Bobenheim-Roxheim, both of Germany

[73] Assignee: BASF Aktiengesellschaft, Ludwigshafen (Rhine), Germany

[22] Filed: Mar. 28, 1973

[21] Appl. No.: 345,504

[30] Foreign Application Priority Data
Apr. 8, 1972  Germany............................ 2216974

[52] U.S. Cl.............................. 260/340.7; 260/338; 260/340.9; 260/468 R; 260/486 R; 260/488 R; 260/488 H; 260/586 C; 260/590 C; 260/593 R; 260/594

[51] Int. Cl.²................... C07C 41/00; C07C 45/00

[58] Field of Search............ 260/586 R, 590, 593 R, 260/594, 596, 598, 599, 601 R, 602, 593, 338, 340.7, 340.9, 468 R, 486 R, 488 R, 488 H, 586 C, 590 C

[56] References Cited
UNITED STATES PATENTS

| 2,064,254 | 12/1936 | Fuchs................................ 260/593 R |
| 2,697,730 | 12/1954 | Mecorney et al................... 260/596 |
| 3,047,630 | 7/1962 | Addy................................ 260/593 R |
| 3,479,403 | 11/1969 | MacLean............................ 260/596 |
| 3,781,307 | 12/1973 | Chabardes et al.............. 260/586 R |

FOREIGN PATENTS OR APPLICATIONS 2,028,350  6/1969  Germany........................ 260/586 R

OTHER PUBLICATIONS

Pines et al., "J. Am. Chem. Soc.", Vol. 82, pp. 2471–2494, (1960).
Ipatieff et al., "J. Org. Chem.", Vol. 7, pp. 189–198, (1942).

*Primary Examiner*—Norman Morgenstern
*Attorney, Agent, or Firm*—Johnston, Keil, Thompson & Shurtleff

[57] ABSTRACT

A process for the production of high molecular weight unsaturated ketones by alkylation of low molecular weight α,β-unsaturated ketones with an allyl alcohol at elevated temperature in the presence of an acid catalyst. The products are intermediates for the production of various natural substances and perfumes such as the damascenones, damascones or natural dyes such as zeaxanthin, rhodoxanthin or xanthophyll.

8 Claims, No Drawings

PRODUCTION OF HIGH MOLECULAR WEIGHT UNSATURATED KETONES

The invention relates to a process for the production of high molecular weight unsaturated ketones by alkylation of α,β-unsaturated low molecular weight ketones with allyl alcohols at elevated temperatures in the presence of acid catalysts.

Methods for the condensation of low molecular weight ketones with aliphatic alcohols are described in a publication by V. N. Ipatieff et al (J. Org. Chem. 7 (1942), 189 to 198), in U.S. Pat. Nos. 2,064,254, 2,697,730 and 2,725,400 and in German Laid-Open Specification DOS No. 2,028,350. In these methods a temperature range of from 200° to 400°C and the presence of catalysts having a dehydrogenating action are preferred. Owing to the high reaction temperatures only very stable ketones can be prepared in this way. French Patent No. 1,582,621 further discloses the reaction of ketones with primary alcohols in the presence of a basic compound and a precious metal catalyst. Essentially the carbon atom of the ketone which is in the α-position is alkylated by the alcohol in the prior art methods.

It has now been found that surprisingly a high molecular unsaturated ketone of the general formula (I):

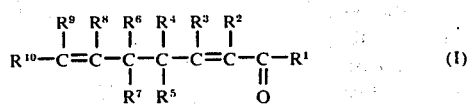

in which
R$^1$ is alkyl of one to four carbon atoms, a cycloaliphatic group or phenyl or together with R$^4$ or R$^5$ is an alkylene which may bear alkyl as substituent;
R$^2$, R$^3$, R$^4$, R$^6$, R$^7$ and R$^8$ is each hydrogen or alkyl of one to four carbon atoms;
R$^5$ is hydrogen or a saturated or unsaturated, branched or linear aliphatic, cycloaliphatic or cycloaliphatic-aliphatic hydrocarbon radical of one to 12 carbon atoms; or together with R$^4$ is alkylidene of one to 12 carbon atoms;
R$^9$ is alkyl of one to four carbon atoms; and
R$^{10}$ is a saturated or unsaturated, branched or linear aliphatic, cycloaliphatic or cycloaliphatic-aliphatic hydrocarbon radical of one to 12 carbon atoms which may also contain oxygen in the form of ether, acetal or ester groupings, or an unsubstituted or alkyl-substituted phenyl;
and when R$^{10}$ is unsubstituted or substituted phenyl R$^9$ may also be hydrogen can be prepared by a simple method and in good yields by reacting an allyl alcohol of the formula (II):

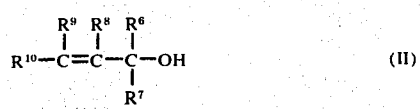

in which R$^6$ to R$^{10}$ have the meanings given above, at a temperature of from 100° to 350°C in the presence of an acid catalyst in the liquid phase with an α,β-unsaturated ketone of the formula (III):

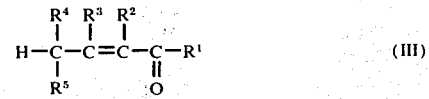

in which R$^1$ to R$^5$ have the meanings given above.

It is surprising that in the reaction of an α,β-unsaturated ketone with an allyl alcohol of formula (II) it is not alkylation of the α-carbon atom but selective alkylation of the γ-carbon atom which takes place even when the carbon atom in the α-position to the carbonyl group bears a hydrogen atom.

It is also surprising that under the reaction conditions of the invention a number of high molecular weight polyunsaturated ketones can be obtained in good yields which hitherto could only be obtained by very expensive methods.

It is preferred to use as starting materials allyl alcohols of the formula (II) in which R$^6$ to R$^8$ are hydrogen or methyl, R$^9$ is methyl and R$^{10}$ is a saturated or unsaturated, branched or linear, aliphatic or cycloaliphatic-aliphatic hydrocarbon radical of one to twelve carbon atoms which may contain oxygen in the form of an ether, acetal or ester grouping or phenyl, and in this case R$^9$ may also be hydrogen.

The preferred allyl alcohols have a total of from about five to 20, particularly from six to 15 carbon atoms.

The following are examples:
3-methyl-2-buten-1-ol, 3-methyl-2-penten-1-ol, cyclic acetals of 4-hydroxy-2-methyl-2-buten-1-al, 4-methoxy-3-methyl-2-buten-1-ol, 4-acetoxy-3-methyl-2-buten-1-ol, 4-methyl-3-penten-2-ol, 3,4,4-trimethyl-2-penten-1-ol, 1,1,3-trimethyl-3-cyclohexan-5-ol, geraniol, nerol, farnesol, ionylideneethanol, cinnamyl alcohol and 3-methylcinnamyl alcohol.

As the α,β-unsaturated ketones of the formula (III) it is preferred to use ketones in which R$^1$ is methyl or ethyl or together with R$^5$ is alkylene which may bear methyl as substituent, R$^2$ to R$^4$ are hydrogen, methyl or ethyl and R$^5$ is hydrogen or a saturated or unsaturated, branced or unbranched aliphatic or cycloaliphatic-aliphatic hydrocarbon radical of one to twelve carbon atoms or together with R$^4$ is alkylidene of one to ten carbon atoms.

The ketones of formula (III) which it is preferred to use generally have from five to 20, particularly from six to 12, carbon atoms. Examples are: 3-penten-2-one, 4-methyl-3-hexen-2-one, 4-ethyl-3-hexen-2-one, 5-methyl-4-hexen-3-one, 5-methyl-4-hepten-3-one, 6-methyl-3-hepten-2-one, 6-methyl-3,5-heptadien-2-one, 4,8-dimethyl-3,7-nonadien-2-one, pseudoionone and 4,8,12-trimethyl-3,7,11-tridecatrien-2-one and particularly mesityl oxide and isophorone.

The process of the invention proceeds particularly advantageously when the starting material is an α,β-unsaturated ketone which on the carbon atom in the β-position to the carbonyl group has a branch junction, i.e. ketones of the formula (III) in which R$^3$ is not hydrogen but a hydrocarbon radical of one to 11 carbon atoms, preferably methyl.

The starting material may be used in a stoichiometric proportion. It is advantageous to use the more stable component in a one to four molar excess.

Suitable acid catalysts include practically all compounds which can split off protons or which can cause an acid reaction, i.e. a pH of from 0 to 6.9, by hydrolysis when dissolved in water and which in the amount necessary for catalysis do not otherwise attack the reactants. Naturally those skilled in the art will avoid the use of acids which may decompose under the reaction conditions. Mineral acids, acid salts, heterogeneous acid catalysts and organic acids are all suitable.

Examples of mineral acids are: sulfuric acid, phosphoric acid, hydrogen halides, nitric acid, sulfurous acid, phosphorous acid, perchloric acid, boric acid and silicic acid.

Examples of suitable acid salts are the salts of polybasic acids in which the dissociatable hydrogen is only partially replaced by metal such as sodium bisulfate, potassium bisulfate, primary sodium phosphate and sodium bisulfite.

Suitable acid salts also include the salts of strong acids with weak bases such as zinc chloride, aluminum chloride and boron trifluoride.

Examples of heterogeneous acid catalysts are catalysts such as silica gel, sodium bisulfate on activated carbon and acid aluminum oxide.

The following groups are examples of suitable organic acids; aliphatic monocarboxylic acids such as formic acid, acetic acid, propionic acid, butyric acid, acrylic acid, methacrylic acid, dimethylacrylic acid, chlorinated acetic acids and lactic acid;

cycloaliphatic monocarboxylic acids such as cyclohexanoic acid; araliphatic carboxylic acids such as cinnamic acid and phenylacetic acid;

aromatic monocarboxylic acids such as benzoic acid, naphthoic acid, salicylic acid, p-anisic acid and nicotinic acid;

aliphatic dicarboxylic or tricarboxylic acids such as oxalic acid, malonic acid, succinic acid, adipic acid, citric acid, malic acid and maleic acid;

aromatic dicarboxylic and tricarboxylic acids such as phthalic acid and terephthalic acid;

aromatic sulfonic acids such as benzenesulfonic acid and p-toluenesulfonic acid; and phenols such as phenol, cresols, hydroquinone, chlorobenzenes, trichlorophenols, nitrophenols and 2,4-dinitrophenol.

The type of acid used as catalyst is not critical provided the acid does not otherwise attack the reaction partners under the reaction conditions. It is only essential that a certain concentration of hydrogen ions which is not too high should be present in the reaction mixture. It is best to use a reaction mixture to which an amount of acid has been added so that one of the commercial pH indicator papers when dipped into the reaction mixture indicates a pH of from about 1 to 6, preferably from 2 to 5. The amount of acid used as catalyst thus depends on the strength of the acid. i.e. the degree of dissociation of the acid, because when the medium is too strongly acid a side reaction by etherification of the allyl alcohol takes place and in too weakly acid medium the formation of ethers takes place as a side reaction by the addition of allyl alcohol to the double bond of the unsaturated ketone.

The reaction of the invention proceeds particularly advantageously when an allyl alcohol of formula (II) is reacted with the unsaturated ketone of formula (III) in the presence of from 0.01 to 5% by weight, preferably from 0.1 to 3% by weight (based on the sum of the reactants) of an acid having a pK value of from about 1 to 5.

The following are examples of preferred acids having a pK value of from about 1 to 5:
formic acid, acetic acid, propionic acid, benzoic acid, acrylic acid, dimethylacrylic acid, oxalic acid, malonic acid, succinic acid and adipic acid.

When using the stronger acids, i.e. acids of a pK value of less than 1, only small amounts of acid should be used as catalyst because the desired reaction products are sensitive to acid.

The reaction of the invention also proceeds advantageously when it is carried out in the presence of from 0.001 to 1% by weight, particularly from 0.005 to 0.5% by weight, based on the sum of the reactants, of an acid having a pK value less than 1.

Examples of acids having a pK value of less than 1 are: sulfuric acid, phosphoric acid, hydrogen halides, p-toluenesulfonic acid and the chloroacetic acids.

The use of very weakly acid compounds, i.e. acids having a pK value of more than 7 such as the phenols as catalyst is less advantageous.

In order to carry out the process the starting compounds are heated in the presence of an acid catalyst for the duration of the reaction at a temperature of from 100° to 350°C, preferably from 130° to 290°C, if necessary at superatmospheric pressure.

The reaction proceeds particularly advantageously when the water formed in the reaction is withdrawn by adding water-binding agents such as orthoesters from the reaction equilibrium or the water is removed from the reaction mixture continuously as an azeotropic mixture by injecting a low boiling point hydrocarbon such as pentane, hexane or cyclohexane as entrainer.

Reactants may themselves be used as entrainers for water.

The reaction may be carried out in the absence of solvents or in the presence of a solvent.

Suitable solvents include aliphatic and aromatic hydrocarbons which are inert under the reaction conditions such as pentane, hexane, benzene, toluene and also ethers, for example tetrahydrofuran, dioxane or ethylene glycol monomethyl ether and particularly strongly polar solvents such as acetonitrile, dimethylformamide or dimethyl sulfoxide.

The solvent is used in an amount which is from twice to five times the amount of the starting components taken together.

The process may be carried out batchwise in a stirred vessel or a vibrated autoclave or continuously in a reactor or cascade of reactors. Atmospheric pressure or a pressure of from 1 to 250 atmospheres may be used. The reaction conditions are chosen in all cases so that the reaction takes place in the liquid phase.

The reaction period for the reaction of the invention is from 5 minutes to 20 hours, preferably from 30 minutes to 10 hours. depending on the reaction temperature and the catalyst used.

The reaction mixture is worked up generally by fractional distillation.

It is possible by means of the process of the invention in a simple manner and with good yields to obtain a number of high molecular weight $\alpha,\beta$-unsaturated ketones which hitherto could be prepared only by very expensive methods and which have achieved significance as valuable precursors and intermediates for the production of various natural substances and perfumes such as damascenones, damascones or natural dyes such as zeaxanthin, rhodoxanthin or xanthophyll.

Thus for example β-damascone may be obtained from the 4,8-dimethyl-3,7-nonadien-2-one (obtained according to Example 1 or 2) by acid-catalyzed cyclization and reaction of the 1-acetyl-2,6,6-tri-methyl-1-cyclohexene thus obtained with acetaldehyde. α-damascone is obtained from β-damascone by isomerization and damascenone is obtained by reaction with N-bromosuccinimide and elimination of HBr.

The following Examples illustrate the invention. The parts specified in the Examples are by weight unless stated otherwise; parts by volume are related thereto as the liter to the kilogram.

EXAMPLE 1

800 parts of mesityl oxide, 200 parts of 3-methyl-2-buten-1-ol (prenol) and 2 parts of formic acid are heated at 250°C for 3 hours in a vibrated autoclave holding 2500 parts by volume at a pressure of 60 atmospheres. The reaction mixture is worked up by distillation and gives 190 parts of 4,8-dimethyl-3,7-nonadien-2-one having a boiling point of 60° to 62°C at 0.2 mm. The yield is 78% of theory at a conversion of 63% based on prenol.

EXAMPLE 2

A mixture of 400 parts of mesityl oxide, 100 parts of prenol and 5 parts of 3,3-dimethylacrylic acid is heated for 4 hours at a pressure of 1.9 atmospheres and a temperature of 175°C in a still provided with means for removing water. The water formed is removed azeotropically. The reaction mixture is worked up. 85 parts of 4,8-dimethyl-3,7-nonadien-2-one is obtained. This is equivalent to a yield of 86% of theory at a conversion of 51% based on prenol.

EXAMPLE 3

800 parts of mesityl oxide and 200 parts of geraniol have 1 part of oxalic acid added to them and the mixture is heated for three hours at a pressure of 50 atmospheres in the vibrated autoclave described in Example 1 at a temperature of 230°C. The reaction mixture is worked up by distillation. 141 parts of 4,8,12-trimethyl-3,7,11-tridecatrien-2-one is obtained with a boiling point of 92° to 94°C at $10^{-4}$ mm. The yield is 81% of theory at a conversion of 57% based on geraniol.

EXAMPLE 4

A mixture of 800 parts of isophorone, 400 parts of prenol and 6 parts of formic acid is heated for five hours at 30 atmospheres pressure at 220°C. The reaction mixture is then worked up by distillation. 470 parts of 1-(3'-methyl-2'-buten-1'-yl)-2,2,6-trimethylcyclohex-5-en-4-one is obtained with a boiling point of 75° to 76°C at $10^{-4}$ mm. The yield is 83% of theory at a conversion of 59% based on prenol.

EXAMPLE 5

A mixture of 400 parts of isophorone, 100 parts of 2-methyl-4-hydroxy-2-buten-1-al-(2',2'-dimethylpropylene)-acetal and 5 parts of 3,3-dimethylacrylic acid is heated for 5 hours in a still with superposed means for removing water and at a bottoms temperature of 190°C, water formed during the reaction being removed continuously by injecting pentane. The reaction mixture after having been worked up gives 82.5 parts of 2-methyl-2-buten-4-(2',2',6'-trimethyl-4'-oxocyclohex-5'-en-1'-yl)-1-al-(2',2'-dimethylpropylene)-acetal. This product has a boiling point of 140° to 143°C at $10^{-4}$ mm. The yield obtained is 77% of theory (based on 2-methyl-4-hydroxy-2-buten-1-al-(2',2'-dimethylpropylene)-acetal) at a conversion of 65%.

EXAMPLE 6

A mixture of 200 parts of mesityl oxide, 200 parts of geraniol and 400 parts of tetrahydrofuran has 0.01 part of p-toluenesulfonic acid added to it and the whole is heated for 3 hours at 200°C at 50 atmospheres pressure. The reaction mixture is distilled and 133 parts of 4,8,12-trimethyl-3,7,11-tridecatrien-2-one is obtained. At a conversion of 52% the yield is 78% of theory based on geraniol.

EXAMPLE 7

500 parts of isophorone and 300 parts of prenol are dissolved in 400 parts of toluene and heated with 0.1 part of concentrated phosphoric acid (89%) for 2 hours at 190°C and a pressure of 45 atmospheres. The reaction product gives 300 parts of 1-(3'-methyl-2'-buten-1'-yl)-2,2,6-trimethylcyclohex-5-en-4-one. At a conversion of 55% the yield is 76% of theory based on prenol.

We claim:
1. A process for the production of high molecular weight unsaturated ketones of the formula

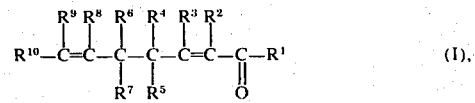  (I), in which:
R¹ is alkyl of one to four carbon atoms, a cycloaliphatic hydrocarbon radical or phenyl;
R¹, R⁴ and R⁵ together may be alkylene which may bear alkyl as a substitute;
R², R³, R⁴, R⁶, R⁷ and R⁸ are hydrogen or alkyl of one to four carbon atoms;
R⁵ is hydrogen or a saturated or unsaturated, branched or unbranched aliphatic, cycloaliphatic or cycloaliphatic-aliphatic hydrocarbon radical of one to 12 carbon atoms, or together with R⁴ may form alkylidene of one to twelve carbon atoms;
R⁹ is alkyl of one to four carbon atoms; and
R¹⁰ is a saturated or unsaturated, branched or unbranched, aliphatic cycloaliphatic or cycloaliphatic-aliphatic hydrocarbon radical of one to 12 carbon atoms which may also contain other than hydrogen and carbon atoms only oxygen in the form of an ether, acetal or ester grouping, or unsubstituted or alkyl-substituted phenyl, and
when R¹⁰ is unsubstituted or substituted phenyl R⁹ may also denote hydrogen, which process comprises:
reacting an allyl alcohol of the formula

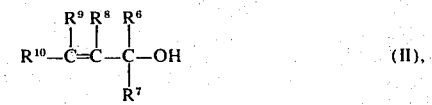  (II), in which R⁶ to R¹⁰ have the meanings given above, at a temperature of from 100° to 350°C. in the presence of a catalytically effective amount of an acid having a pK value up to about 7 as the sole catalyst and in the liquid phase with a α,β-unsaturated ketone of the formula

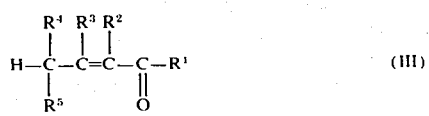

in which $R^1$ to $R^5$ have the meanings given above.

2. A process as claimed in claim 1, wherein the allyl alcohol of formula (II) is reacted in the presence of from 0.01 to 5% by weight based on the sum of the reactants of an acid having a pK value of about 1 to 5 with the unsaturated ketone of the formula (III).

3. A process as claimed in claim 2 wherein the said percentage is from 0.1 to 3% by weight.

4. A process as claimed in claim 1 wherein the allyl alcohol of formula (II) is reacted with the unsaturated ketone of formula (III) in the presence of from 0.001 to 1% by weight, based on the sum of the reactants of an acid having a pK value of less than 1.

5. A process as claimed in claim 4 wherein the said percentage is from 0.005 to 0.5% by weight.

6. A process as claimed in claim 1 wherein the allyl alcohol of formula (II) is reacted with the unsaturated ketone of formula (III) at a temparature of from 130° to 290°C.

7. A process as claimed in claim 1 wherein water formed in the reaction is continuously removed from the reaction mixture.

8. A process as claimed in claim 1 wherein the allyl alcohol of formula (II) is reacted with the unsaturated ketone of formula (III) at a pH of from 1 to 6.

* * * * *